United States Patent [19]

Warriner

[11] Patent Number: Plant 6,577

[45] Date of Patent: Jan. 31, 1989

[54] ROSE PLANT JACRIS

[75] Inventor: William A. Warriner, Tustin, Calif.

[73] Assignee: Jackson & Perkins Co., Medford, Oreg.

[21] Appl. No.: 922,634

[22] Filed: Oct. 24, 1986

[51] Int. Cl.[4] ..... A01H 5/00

[52] U.S. Cl. ..... Plt./1

[58] Field of Search ..... Plt./1, 6

*Primary Examiner*—Robert E. Bagwill

*Attorney, Agent, or Firm*—Majestic, Gallagher, Parsons & Siebert

[57] ABSTRACT

A shrub rose variety having vigorous, upright growth habit, profusion of single red flowers, glossy green foliage and ability to easily root from hardwood cuttings.

2 Drawing Sheets

This present invention relates to a new and distinct variety of rose plant of the shrub class which was originated by crossing the variety Sunsprite, U.S. Plant Pat. No. 3,509, with an unnamed variety.

The primary objective of this breeding was to produce a new rose variety with a very upright habit, distinctive flower and good plant vigor. This objective was substantially achieved along with other desirable improvements as evidenced by the following unique combination of characteristics which are outstanding in the new variety and which distinguish it from its parents as well as from all other varieties of which I am aware:

1. A simple flower of five petals;
2. A bright red flower with distinctive yellow eye;
3. Glossy, green foliage;
4. Upright growth habit;
5. Excellent rooting ability from hardwood cuttings; and
6. Powdery mildew susceptibility.

Asexual reproduction of this new variety by cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Sunsprite, U.S. Plant Pat. No. 3,509.

*Pollen parent.*—Unnamed variety.

Classification:

*Botanical.*—Rosa hybrid.

*Commercial.*—Shrub.

FLOWER

Observations made from specimens grown in a greenhouse at Irvine, Calif. in Sept., 1986.

Blooming habit: Continuous.

Bud:

*Size.*—1" when petals start to unfurl.

*Form.*—Pointed ovoid.

*Color.*—When sepals first divide, Red Group 44B; when half blown, upper side of petals Red Group 44A to B with a distinctive yellow half moon at the petal base (Yellow Group 6A to B); lower side of petals, a lighter shade of red (Red Group 43A) with a yellow base at the point of attachment (Yellow Group 6B).

*Sepals.*—Color: Green Group 138C. Three appendaged sepals heavily appendaged. Two unappendaged sepals hairy edged.

*Receptacle.*—Color: Green Group 138, sometimes tinged with red. Shape: Apple. Size: Small. Surface: Smooth.

*Peduncle.*—Length: Medium. Surface: Rough, prickly. Color: Bronzy. Strength: Stiff.

Open bloom:

*Size.*—Medium to small. Average open size 3".

*Borne.*—Singly.

*Stems.*—Medium, strong.

*Form.*—When first open, flat. Permanence: Retains its form to the end.

*Petalage.*—Number of petals under normal conditions: 5.

*Color.*—Center of flower: Upper side of petals, Red Group 44A to B with a distinctive yellow half moon at the base of the petals (Yellow Group 6A to B); reverse side of petals, Red Group 43A with a yellow base at the point of attachment (Yellow Group 6B). Base of petals, Yellow Group 6A to B. Major color: Red Group 44A to B.

*Variegations.*—None.

*Discoloration.*—General tonality at end of first day: No change. Third day: Under warm conditions, there is some fading.

*Fragrance.*—Moderate.

Petals:

*Texture.*—Thick.

*Shape.*—Round.

*Form.*—Flat.

*Arrangement.*—Regular. Petaloids in center, none.

*Persistence.*—Drop off cleanly.

*Lastingness.*—On the plant, fair.

Reproductive parts:

*Anthers.*—Large. Color: Yellow. Arrangement: Regular around styles.

*Filaments.*—Color: Yellow.

*Pollen.*—Gold yellow.
*Styles.*—Color: Red.
*Stigmas.*—Color: Greenish White.

PLANT

Form: Shrub.
Growth: Vigorous, upright.
Foliage: Number of leaflets on normal mid-stem leaves: 5 to 7.
*Size.*—Medium.
*Quantity.*—Normal.
*Color.*—New foliage: Reddish. Old foliage: Green Group 139A.
Leaflets:
*Shape.*—Broadly oval pointed.
*Texture.*—Smooth.
*Edge.*—Serrated.
*Serration.*—Single, medium.
*Petiole.*—Rachis: Color: Reddish. Underside: Rough with prickles.
*Stipules.*—Long, bearded.

*Disease resistance.*—Susceptible to mildew, under normal growing conditions at Irvine, Calif.
Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Straight.
*Color when young.*—Red.
Small prickles:
*Quantity.*—On main stalks, none. On laterals, few.
*Color.*—Reddish.

I claim:

1. A new and distinct variety of rose plant of the shrub class, substantially as herein shown and described, characterized particularly as to novelty by the unique combination of its vigorous, upright growth habit, profusion of single red flowers, glossy green foliage and its ability to easily root from hardwood cuttings.

* * * * *

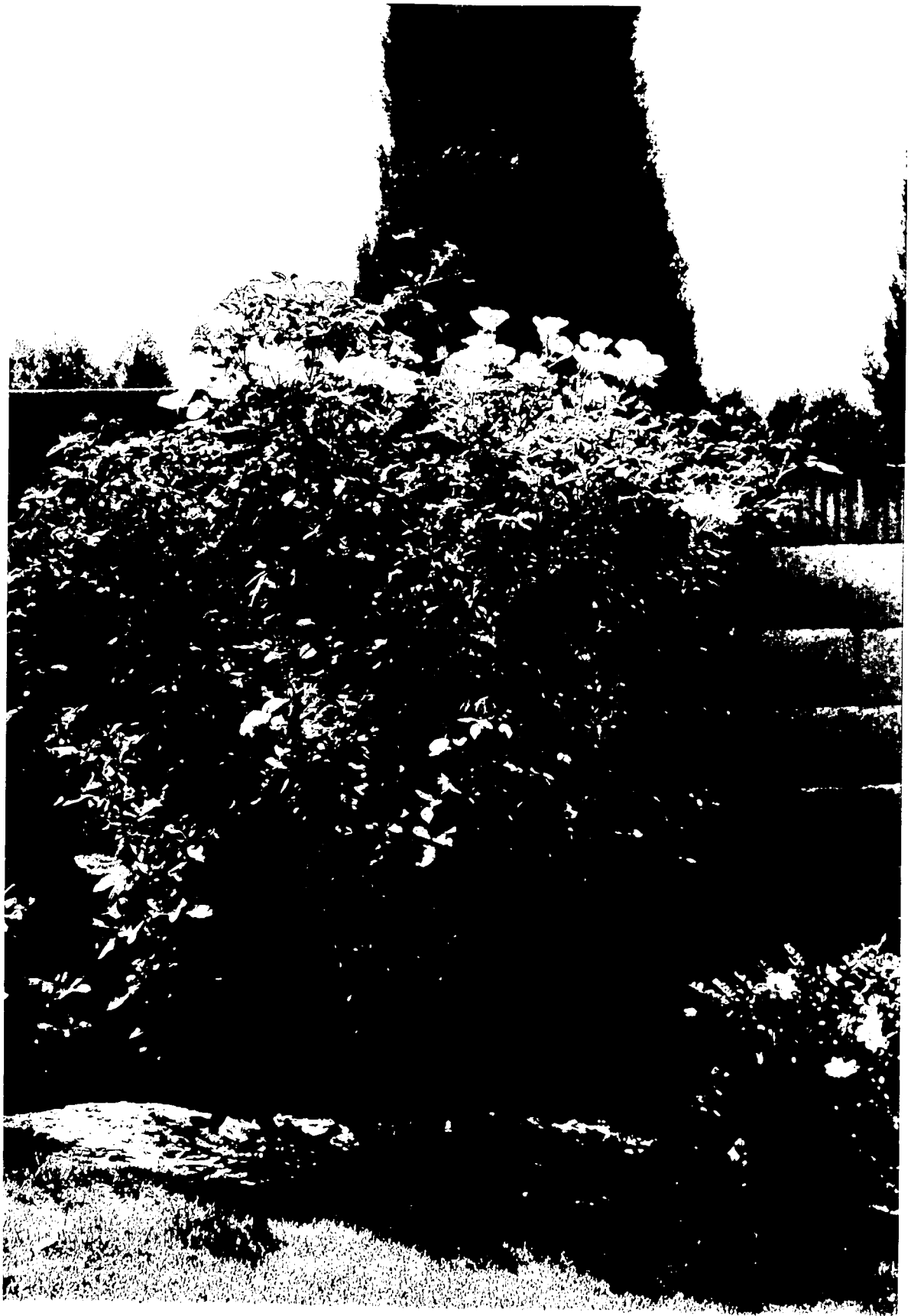

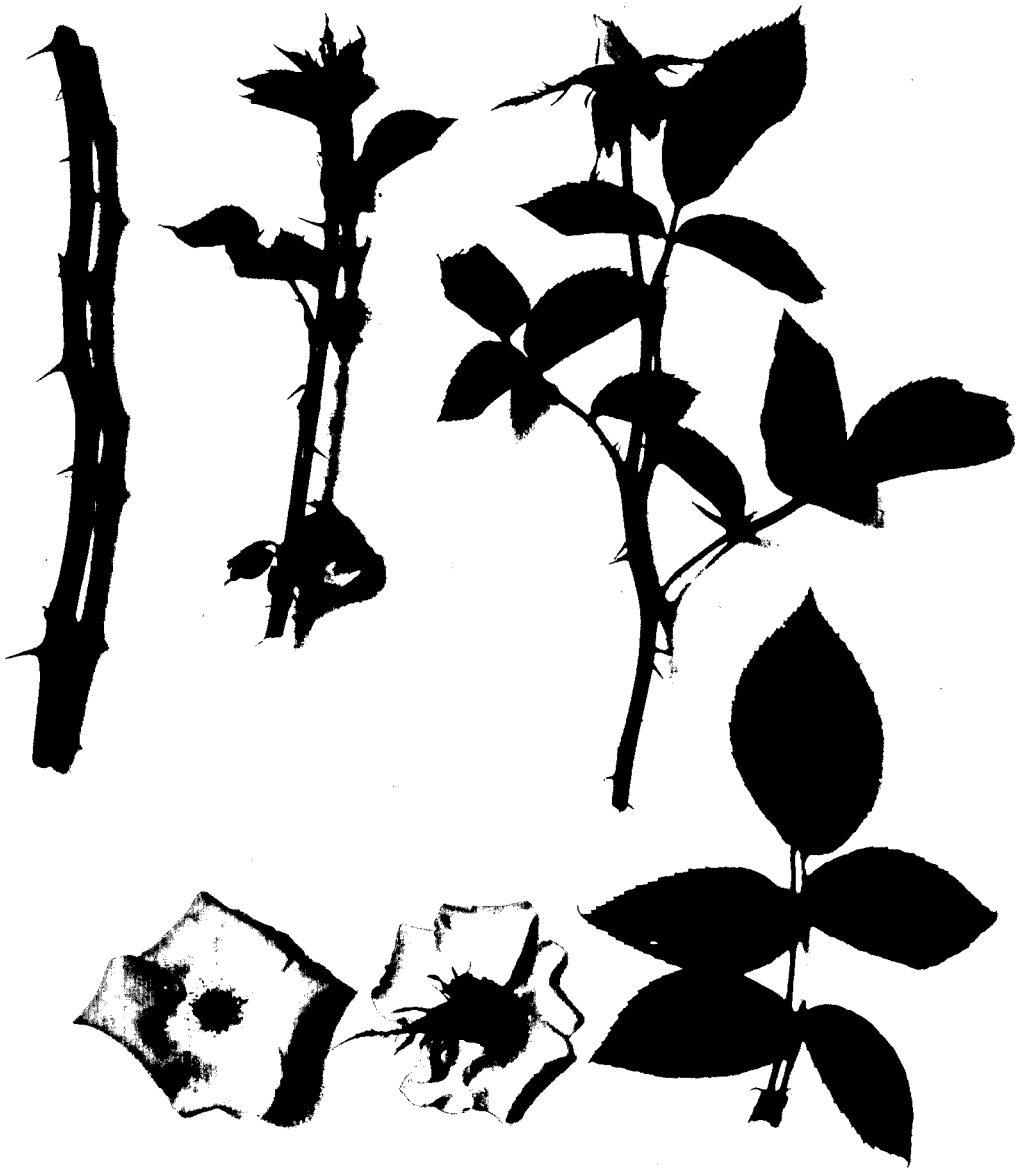
JACRIS